United States Patent
Brougham et al.

(10) Patent No.: US 8,883,122 B2
(45) Date of Patent: Nov. 11, 2014

(54) NANOPARTICLE CLUSTERS FORMED FROM INDIVIDUAL NANOPARTICLES OF TWO OR MORE TYPES

(75) Inventors: Dermot Brougham, Dublin (IE); Carla Meledandri, Murrysville, PA (US); Jecek Stolarczyk, Skoczow (PL); Tsedev Ninjbadgar, Dublin (IE)

(73) Assignee: Dublin City University, Dublin (IE)

( * ) Notice: Subject to any disclaimer, the term of this patent is extended or adjusted under 35 U.S.C. 154(b) by 24 days.

(21) Appl. No.: 13/517,023

(22) PCT Filed: Dec. 17, 2010

(86) PCT No.: PCT/EP2010/070121
§ 371 (c)(1),
(2), (4) Date: Jun. 18, 2012

(87) PCT Pub. No.: WO2011/073411
PCT Pub. Date: Jun. 23, 2011

(65) Prior Publication Data
US 2012/0282182 A1    Nov. 8, 2012

(30) Foreign Application Priority Data
Dec. 17, 2009    (GB) .................................. 0922052.6

(51) Int. Cl.
*A61K 9/50*    (2006.01)
*B82Y 5/00*    (2011.01)
*A61K 49/18*   (2006.01)
*B82Y 30/00*   (2011.01)
*A61K 41/00*   (2006.01)

(52) U.S. Cl.
CPC . *B82Y 30/00* (2013.01); *B82Y 5/00* (2013.01); *A61K 49/1839* (2013.01); *A61K 41/0052* (2013.01); *A61K 49/1887* (2013.01)
USPC .......................................................... 424/9.1

(58) Field of Classification Search
CPC .................................................. A61K 41/0052
USPC .......................................................... 424/9.1
See application file for complete search history.

(56) References Cited

FOREIGN PATENT DOCUMENTS

EP    1 935 436 A1    6/2008
WO    2008/071742 A1    6/2008

OTHER PUBLICATIONS

Pinna, N. et al., "Magnetite Nanocrystals: Nonaqueous Synthesis, Characterization, and Solubility", Mar. 30, 2005, Chem. Mater. 2005, 17, 3044-3049.
International Search Report, mailed Mar. 30, 2011, for PCT/EP2010/070121, 4 pages.
Brust et al., "Synthesis of Thiol-derivatised Gold Nanoparticles in a Two-phase Liquid-Liquid System," J. Chem. Soc., Chem. Commun., pp. 801-802, 1994.
Caruntu et al., "Attachment of Gold Nanograins onto Colloidal Magnetite Nanocrystals," Chem. Mater. 17:3398-3402, 2005.
Stolarczyk et al., "Controlled Growth of Nanoparticle Clusters through Competitive Stabilizer Desorption," Angew. Chem. Int. Ed. 48:175-178, 2009.
Sun et al., "Size-Controlled Synthesis of Magnetite Nanoparticles," JACS 124:8204-8205, 2002.

*Primary Examiner* — Jake Vu
(74) *Attorney, Agent, or Firm* — Seed IP Law Group PLLC

(57) ABSTRACT

Nanoparticle clusters are described. In particular nanoparticle clusters formed from two or more individual nanoparticles of different types are described and methods for fabricating such nanoparticle clusters are further described. These nanoparticle clusters are fabricated by surface activating individual ones of the plurality of nanoparticles by desorption of surfactant molecules from the surface of the coated nanoparticles through exposure of the individual ones of the plurality of nanoparticles to an activating agent.

37 Claims, 9 Drawing Sheets

NANOPARTICLE CLUSTERS FORMED FROM INDIVIDUAL NANOPARTICLES OF TWO OR MORE TYPES

FIELD OF THE INVENTION

The present invention relates to nanoparticle clusters. In particular the invention relates to nanoparticle clusters formed from two or more individual nanoparticles of different types.

BACKGROUND

Nanoparticles are those particles having one or more dimensions of the order of 100 nm or less. Nanoparticles can have different sizes and it is known for a specific type of nanoparticle to have varying size dimensions. It is also known to grow larger nanoparticles from smaller nanoparticles. Growth of individual NPs is usually by addition of atomic/molecular scale components. This can be done either by adding precursor material (seed mediated growth) to the NP suspension in which case there are the same number of nanoparticles at the end of the process as there were at the beginning, or by adding NPs to the NP suspension (Ostwald ripening). In the latter process one set of NPs act as a source of atomic/molecular scale components and that material is then added to the growing NPs In both these processes there is no aggregation of individual nanoparticles. Providing a plurality of individual single nanoparticles of different sizes is different to providing clusters of nanoparticles or nanoparticle clusters. A nanoparticle cluster is the result of two or more nanoparticles binding to one another through a physical or chemical interaction, with the resultant entity being a combination of the two or more individual nanoparticles such that the plurality persists for a timescale long in comparison to the atomic/molecular time scales associated with the process that result in the combination. Within a cluster, it is possible to identify the individual nanoparticles.

Stable suspensions of magnetic nanoparticles (NPs) and of magnetic nanoparticle clusters (NPCs) have great potential biomedical applications. They have been considered as potential drug delivery vehicles which can be localized at a site of interest by application of external magnetic fields. They are currently also being used as contrast agents for magnetic resonance imaging (MRI) as the large magnetic moments, associated in particular with iron-oxide NPs, produce strong magnetic resonance relaxation enhancements which can be used to improve image contrast in body tissues containing the agent.

Despite these beneficial applications, significant challenges remain to fully exploit this biomedical potential. Amongst these are improvement in the control of cluster size, composition and architecture, as these properties largely determine the cluster bio-distribution, drug delivery potential and the molar MRI relaxation rate enhancements (the spin-lattice and spin-spin relaxivities, $r_1$ and $r_2$).

Methods for preparing magnetic NPCs include the reaction of primary NPs with polymers and in situ NP formation and stabilization. In the former approach the surface chemistry of the polymer determines the outcome and so for a given polymer, stable suspensions can usually only be produced at one cluster size, while larger clusters are associated with low NP loading.

A common approach to improve the functionality and stability of magnetic NPs and NPCs is to incorporate noble metals, particularly gold, as Au/FeO nanocomposite materials. The most common architecture involves coating FeO cores in a complete layer, or shell, of gold, producing FeO@Au nanoparticles. The gold shell imparts many favourable properties, largely due to the well established Au—S chemistry, which offers the possibility of conjugating hydrophilic ligands and bioactive molecules. However, control of the thickness of the Au layer remains a challenge and the layer reduces the saturation magnetization of the particles, which greatly reduces the contrast agent potential of core-shell materials.

The preparation of Au NPs conjugated to FeO NPs has also been reported. Negatively charged, 2-3 nm, Au NPs were chemically attached onto amino-siloxane (APTES) coated ~10 nm $Fe_3O_4$ nanoparticles, producing stable ethanol suspensions. This approach was demonstrated to have minimal effect on the saturation magnetization. For application as $T_2$ contrast agents, or as drug delivery vehicles, further steps involving controlled assembly of such particles would be necessary.

There is therefore a need to provide improved mechanisms for providing nanoparticle clusters.

SUMMARY

These problems and others are addressed in accordance with the present teaching by a methodology for generating nanoparticle clusters from two or more different types of individual nanoparticles. The methodology is advantageously employed in the preparation of size-controlled clusters of nanoparticles, or NPCs, whereby it is possible to control the size of the composite entity throughout the growth process. In this way the user can tailor the process to generate clusters of a predefined dimension.

Accordingly, there is provided a method as detailed in claim 1. The invention also provides a method as detailed in other independent claims. Advantageous embodiments are provided in the dependent claims.

BRIEF DESCRIPTION OF THE DRAWINGS

The present invention will now be described with reference to the accompanying drawings in which:

FIG. 4A shows the affect of heating nanoparticle clusters fabricated from particles only of a first type whereas

DETAILED DESCRIPTION OF THE DRAWINGS

Figure 1:
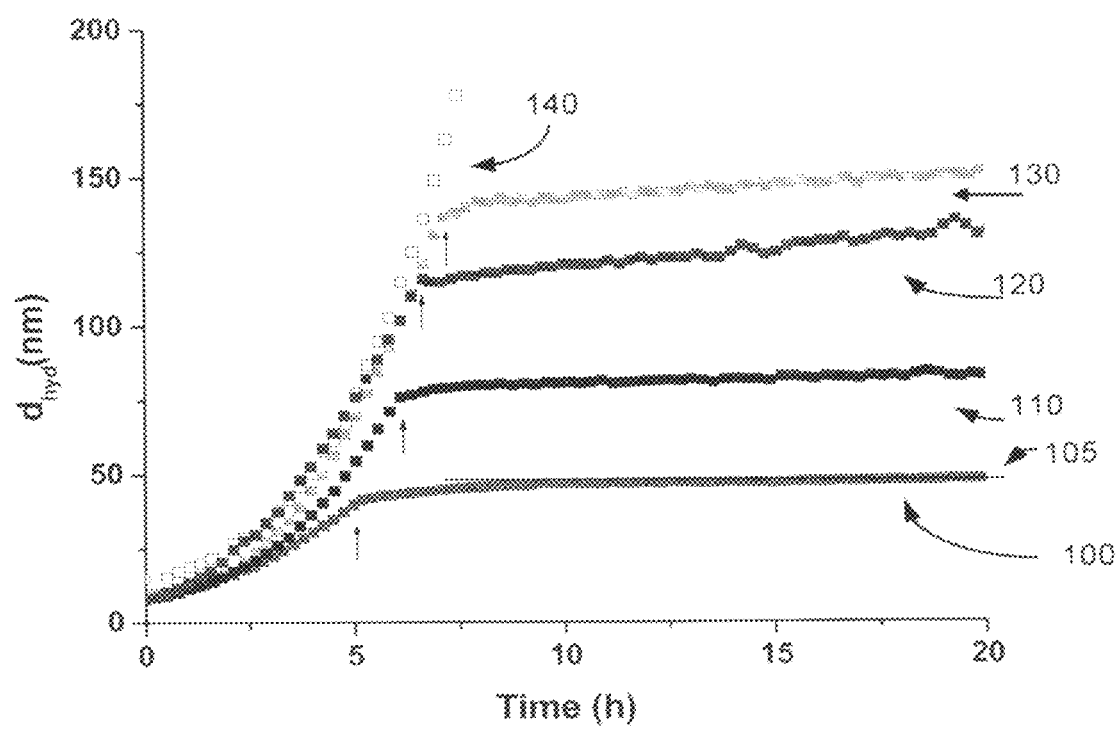
FIG. 1 is shows growth curves for a series of iron oxide nanoparticle cluster suspensions grown under similar conditions over CN-modified silica, with the growth of the nanoparticles clusters being stopped at the times indicated with arrows by the addition of Au NPs in suspension.

An exemplary application of the methodology of the present teaching will now be described to assist the person of ordinary skill in an understanding. In this exemplary arrangement a process for preparation of magnetic fluids comprising monodisperse fatty acid stabilized magnetite nanoparticle clusters, surface decorated with Au nanoparticles (NPs), with size control in the size range 20-150 nm will be described, but it will be appreciated that the present teaching is not to be considered limited to this specific example. The generated nanoparticle clusters (NPCs) are shown as having improved stability and consist of quasi-spherical clusters.

WO 2008071742 co-assigned to the present assignee describes a method for providing nanoparticle clusters of controlled dimensions. The method involves an activation of individual nanoparticles and the subsequent interaction between activated particles to form a cluster. In that teaching, which is incorporated herein by way of reference, individual nanoparticles of the same type in suspension are exposed to an activation source which serves to stimulate the combination of two or more individual nanoparticles to create a nanoparticle cluster. The source of activation is a distinct or separate phase which shows affinity for the surfactant coating on the nanoparticles. In a first arrangement this could be an activation substrate or indeed other activated particles or already formed clusters within the suspension. The source of activation does normally require for the activation source to include a material which provides an activation surface but may be a separate liquid phase or a seed or activated nanoparticle. By removing the suspension from the source of activation it is possible to terminate the further growth of the nanoparticle clusters. In this way a judicious selection of the appropriate time for removal can be useful to provide nanoparticle clusters of a determinable average size with a controlled size distribution. The use of an activated silica substrate was described with an exemplary type being alkyl chain grafted silica or another is cyanated silica. The resultant nanoparticle clusters define structures of two or more nanoparticles with surfactant or other stabiliser material remaining in the boundary between the individual NPs. In such cluster formations, any direct NP to NP contact is only a fraction of the total surface contact area between any two particles.

Similarly to the teaching of that earlier application in this exemplary arrangement, the present invention advantageously employs as an initial starting point heptane, suspensions of fatty-acid coated monodisperse (single sized) 10 nm iron-oxide nanoparticles. These nanoparticles were synthesised in a fashion that will be apparent to the person skilled in the art, such as using the techniques disclosed in *Size-controlled synthesis of magnetite nanoparticies*, Sun S. H., Zeng H., Journal of the American Chemical Society, 124(28), 8204-8205, 2002. These suspensions are known to be stable and unchanging for many months. In effect these coated nanoparticles form the primary particles within the process and have a core with a coating or capping agent provided on the surface thereof, the coating being activatable, so as to result in an activated nanoparticle. However in the initial suspension the nanoparticles are provided in a stabilized form, the stabilization being provided by the capping agent on the surface of the individual nanoparticles. Indeed this process may be used to grow larger NPs from NP seeds by addition of precursor material. It will be appreciated that such a process is different to the current teaching where NPCs are formed by aggregation of NPs or NPCs, not by addition of precursor materials such as atomic iron or oxygen from a simple reagent source, as would be the case in the process termed seed mediated growth.

FIG. 1 shows growth curves for a series of iron oxide NPCs suspensions grown under similar conditions over CN-modified silica (50.2 mg). In this exemplary arrangement monodisperse primary $Fe_2O_3$ NP suspensions in heptane, with $d_{hyd}$ 7.6 nm and PDI in the range 0.15-0.20, were prepared. In this exemplary growth experiment 1.2 mL of a heptane NP suspension, containing 1-3 mM of Fe, was placed in a standard cuvette over 50.2 mg of cyanopropyl-modified 50±20 μm silica particles (Alltech Associates) forming a thin layer at the bottom. The controlled growth of monodisperse clusters of individual nanoparticles, NPCs, by the gradual aggregation of NPs, was then observed over several hours. The rate of growth was sensitively dependent on the starting conditions. It was found that at any time NPC growth could be drastically attenuated by the addition of 50 μL of a heptane suspension of dodecanethiol (DDT) stabilized Au NPs. The Au NP suspensions used had $d_{hyd}$ 7.7 nm, [Au] 0.03 mM, and were prepared using well-known methods as will be apparent to those skilled in the art including those discussed in M. Brust, M. Walker, D. Bethell, D. J. Schiffrin, R. Whyman, *Chem. Comm.* 1994, 7, 801. This concentration corresponds to a Fe:Au mole ratio of approximately 33:1, relative to the initial Fe concentration. In all cases, the FeO NPs were in very large excess at the time the Au NPs were added. At the early stages of the experiment, corresponding to smaller NPCs, growth could be stopped completely with the addition of this concentration of Au NPs.

As is evident from FIG. 1, in accordance with the present teaching the growth of the nanoparticle clusters may be controlled by introduction of a second type of nanoparticle, in this exemplary arrangement gold (Au) nanoparticles. As is evident from the arrows on FIG. 1, the growth of the clusters may be stopped by the addition of Au NPs in suspension. The affect of the Au nanoparticles is evident from the single sample that was not exposed to addition of Au nanoparticles but was allowed to proceed with the resultant continued growth (open marks). A horizontal line is superimposed over the 48 nm NPCs (red squares), to show that even after extended time periods, once the secondary nanoparticle (ie the nanoparticle of the second type) is introduced, that the size of the resultant nanoparticle clusters are relatively stable.

Figure 2:
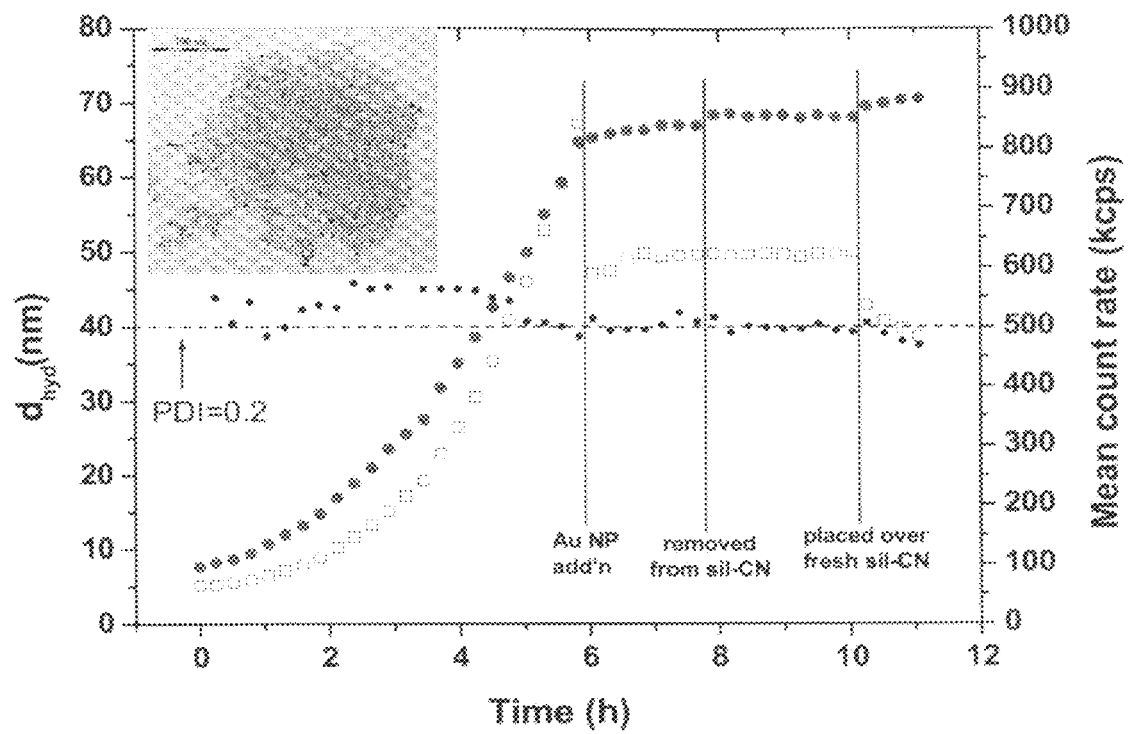
FIG. 2 shows typical growth of clusters of iron oxide NPs observed by DLS; $d_{hyd}$ (filled red circles) and corresponding backscattered light intensity (open blue squares) for a sample placed over CN-modified silica (50.1 mg) with the PDI values being shown to improve slightly over the course of the experiment. Growth was stopped when the $d_{hyd}$ value reached 65 nm by the addition of Au NPs in suspension. The inset shows a TEM image of a typical cluster from an Au-stabilized FeO NPC suspension, the scale bar is 100 nm.
Figure 3:
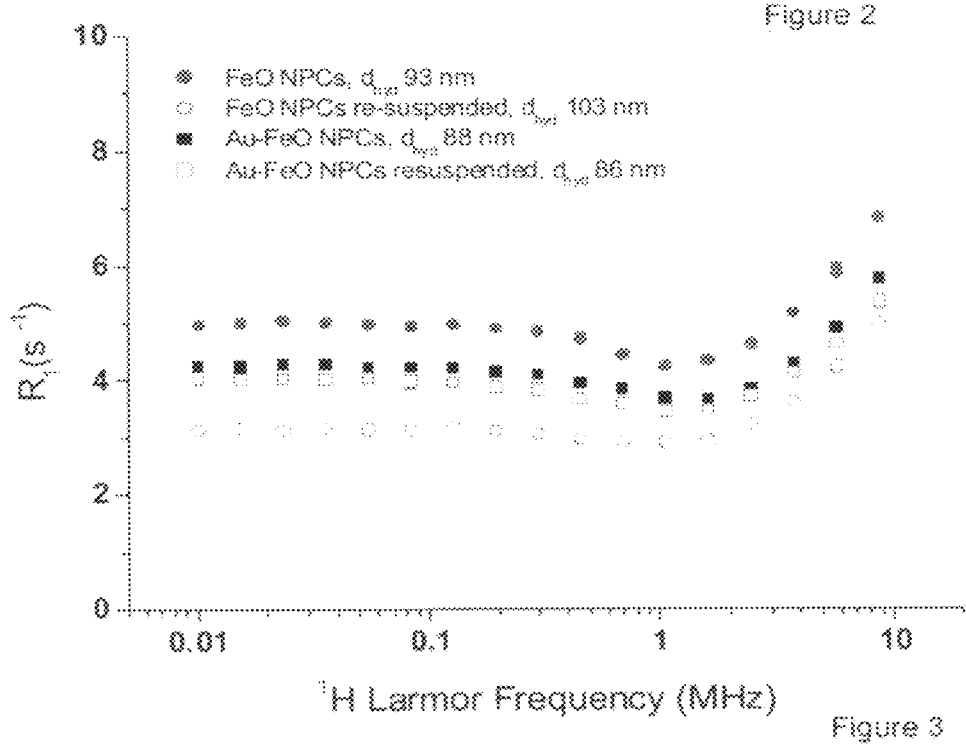
FIG. 3 shows $^1H$ relaxation profiles, recorded at 298 K in heptane, for suspensions of; (i) FeO NPCs, fresh suspension (●) $d_{hyd}$ 93 nm, and after re-suspension (○) $d_{hyd}$ 103 nm, c.60% of the material was re-suspended; (ii) Au—FeO NPCs, fresh suspension (■) $d_{hyd}$ 88 nm, and after re-suspension (□) $d_{hyd}$ 86 nm, c.94% of the material was re-suspended.

As is shown in FIG. 2, the produced nanoparticle composite clusters, i.e. clusters of nanoparticles of a first and second type, may be characterized by light scattering, TEM, and by field-cycling NMR relaxometry, FIG. 3. A micrograph showing a typical cluster is shown as the inset to FIG. 2, this was recorded for a drop of neat NPC suspension, at a time when $d_{hyd}$ was 100 nm, air-dried onto a formvar grid. It reveals the presence of a relatively low concentration of Au NPs (darker spots) on the FeO NPC surface. This confirms production of Au NP decorated FeO NPCs of selected size. At these low Au concentrations very few dispersed Au NPs could be identified on the grid, demonstrating that the Au NPs adsorb onto the NPCs in suspension, and that required dependent on the ultimate application. In this way structures having a composition analogous to an "onion-structure" could be fabricated.

The inclusion of Au NPs in a cluster arrangement already comprising FeO may offer significant advantages for optical detection, for further functionalizing, and by improving the physical characteristics of the suspensions of nanoparticle clusters. In FIG. 3, NMR spin-lattice relaxation rate, R1, data for FeO and Au—FeO NPCs is presented, the rate is determined by the concentration of the particles and their relaxivity according to:

$$R_{1,obs} = R_{1,solv} + r_1[Fe] \quad (1)$$

Where $R_{1,obs}$ (=1/T1,obs) is the measured spin-lattice relaxation rate, $R_{1,solv}$ is rate in the absence of any enhancement, and $r_1$ is the relaxivity which has units of $s^{-1}$ $mM^{-1}$. The frequency dependence of $R_1$ (and hence $r_1$) can be measured by fast-field cycling NMR relaxometry, the shape of the profile being determined by the magnetic properties of the suspended particles. Specifically, the high frequency relaxation is determined by the NP size and the low frequency relaxation is dominated by the magnetocrystalline anisotropy and the saturation magnetization, hence it will be understood that the NMR profile can be used to characterize the magnetic properties of the suspension.

On reaching an average hydrodynamic size of 93 nm a suspension was removed from over the silica. On reaching 88 nm, Au NPs were added to a second separately prepared suspension, and it was subsequently removed from over the silica. The NMR profiles of both suspensions were then recorded. The suspensions were dried under a steady stream of $N_2$. Upon drying, the same volume, 1.2 mL, of heptane was added, the samples were shaken by hand, allowed to stand for 30 minutes, shaken again and re-analyzed. The results presented in FIG. 3 demonstrate that the addition of a partial Au coating has improved the physical robustness of the NPCs. The $d_{hyd}$ and PDI values of the re-suspended Au—FeO NPCs showed no measurable change, while the fact that the shape of the original NMR profile is recovered demonstrates that their magnetic resonance properties are unaffected. Therefore the decrease in the spin-lattice relaxation rate, $R_1$, corresponds to a slight, c.6%, reduction in NPC they are retained during the drying process. In all cases, the NPCs are quasi-spherical, there is no indication of dendritic, or fractal structure, indicating that NPC growth is reaction-, as opposed to, diffusion-limited. While it is not intended to limit the present methodology to any one specific understanding it is believed that the activated silica provides a sink for free oleic acid in suspension, which alters the equilibrium between NP-bound and free surfactant, generating a very low concentration of nanoparticles which are surface activated. The growth of the FeO nanoparticle clusters is terminated by addition of DDT stabilized Au NPs, resulting in functionalized size-selected nanocomposite suspensions.

Careful inspection of FIG. 2 shows that in this case NPC growth was not immediately terminated by the addition of Au NPs, although the data in FIG. 1 suggests that for this suspension growth would also eventually stop. However, in this case, removal of the suspension from over the silica immediately stopped further cluster growth. In addition, the scattered intensity did not change during this time, confirming that there is no significant change in the concentration of the suspended NPCs. The present inventors have found that NPC suspensions in the size range studied are stable, i.e. unchanging by PCS and NMR, for periods of weeks once they have been removed from over the silica. Adding free DDT, in the 1-47 mM range, was observed to have no effect on the growth of iron-oxide NPCs. This confirms that intact DDT-stabilized Au NPs, as opposed to free thiol molecules, are responsible for the effect. This is as expected, given the stability of the Au—S bond, which precludes the action of the Au NPs as a source of free DDT. The present inventors have also observed that re-exposure of the Au—FeO NPCs to fresh silica results in renewed cluster growth—see FIG. 2. Under the conditions of the experiments reported here, a decrease in scattered light intensity was observed during this phase corresponding to precipitation of some of the clusters. However, the possibility of further NP addition after functionalizing the clusters with Au, indicates that the process may be used for the preparation of size-controlled nanostructures with a radially variable or multi-layered composition. Within this context each of the individual layers—or partial layers—of the formed nanoclusters could be varied as concentration. This situation is in stark contrast to that for the unmodified FeO NPCs, where a significant change in size, from 93 to 103 nm was observed, presumably due to shearing of the clusters during re-suspension. Approximately 60% of the material has been recovered, while the change in the shape of the 1H NMR relaxation profile demonstrates a change in the organisation of the NPs within the clusters. The loss of the mid-frequency minimum is known to correspond to an increase in the magnetocrystalline anisotropy energy due to stronger inter-particle interactions. In fact this suspension was not stable; significant aggregation, as indicated by an increase in both $d_{hyd}$ (to 400-800 nm) and PDI, followed by precipitation was observed over a few days. It would appear evident that size control is lost during drying for the non-functionalized clusters and the re-distributed iron-oxide NPs in the suspension have markedly different magnetic properties. In any case it is evident that the nanoparticle clusters formed from individual nanoparticles of the first and second type are advantageously robust when compared to nanoparticles formed from nanoparticles of a first type only.

Alkane-thiols are known to form very high quality monolayers on gold sufaces. A possible mechanism for the cluster formation, although the teaching is not to be construed as being limited to any one specific mechanism, is that the Au NPs physisorb onto the less perfect oleate-coated surface of the FeO NPCs, perhaps filling vacant sites between particles on the growing NPC surface. It will be noted that FIG. 2 clearly shows that the Au NPs have no affinity for each other and hence are dispersed across surface of the clusters.

To investigate the affect of the improved stability of the generated nanoparticle clusters a number of comparisons were conducted between the properties of nanoparticle clusters fabricated from nanoparticles of a first type only—FeO, and nanoparticle clusters formed from first and second types of nanoparticles—FeO and Au.

TABLE 1A

| | Au—FeO NPCs | | |
|---|---|---|---|
| Dilution | Conc (mM) | Z-Avg (nm) | PDI |
| Neat | 1.5 | 85.5 | 0.278 |
| 1:1 | 0.74 | 90.0 | 0.261 |
| 1:2 | 0.49 | 85.5 | 0.221 |
| 1:3 | 0.37 | 86.4 | 0.223 |

TABLE 1B

| | FeO NPCs | | |
|---|---|---|---|
| Dilution | Conc (mM) | Z-Avg (nm) | PDI |
| Neat | 1.2 | 64.7 | 0.197 |
| 1:1 | 0.61 | 76.3 | 0.196 |
| 1:2 | 0.40 | 85.1 | 0.289 |

As is evident the changes in concentration have a more significant affect in the nanoparticle clusters of the first type only (Table 1B) as opposed to those clusters formed from the first and second type (Table 1A).

This stability is also evident when reviewing the affect of time on the PDI and average size measurements.

TABLE 2A

| | Au—FeO NPCs | |
|---|---|---|
| Time (days) | Z-Avg (nm) | PDI |
| 0 | 78.5 | 0.216 |
| 4 | 78.9 | 0.210 |
| 6 | 81.3 | 0.193 |
| 7 | 82.1 | 0.189 |
| 8 | 80.2 | 0.196 |
| 15 | 81.9 | 0.183 |
| 18 | 80.5 | 0.181 |
| 25 | 80.0 | 0.179 |

TABLE 2B

| | FeO NPCs | |
|---|---|---|
| Time (days) | Z-Avg (nm) | PDI |
| 0 | 79.3 | 0.235 |
| 1 | 85.4 | 0.242 |
| 3 | 327 | 0.525 |

Figure 4B:
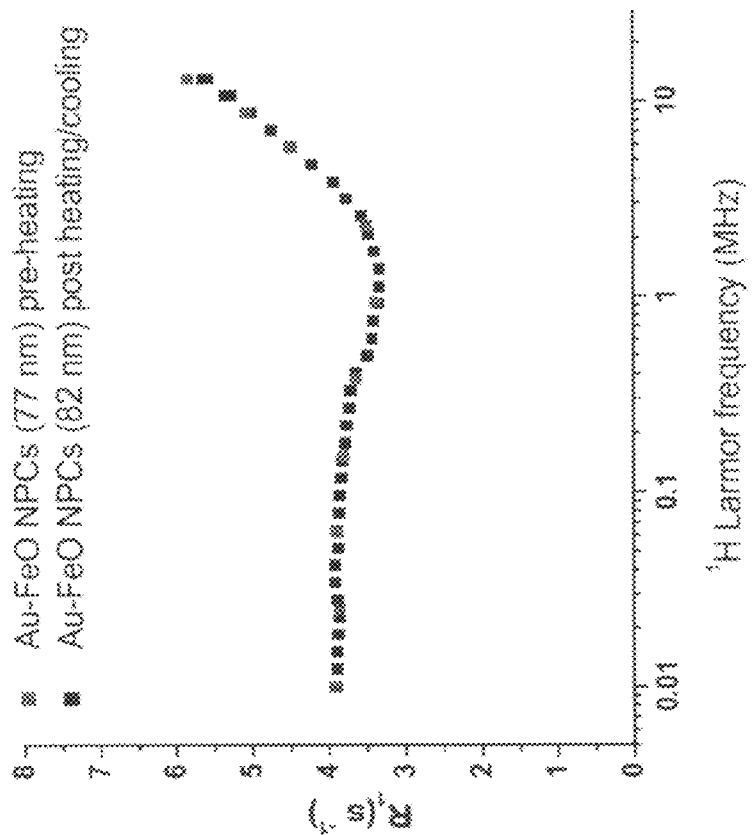
FIG. 4B shows the affect of heating nanoparticle clusters fabricated from the first and second types, in accordance with the present teaching.
Figure 4A:
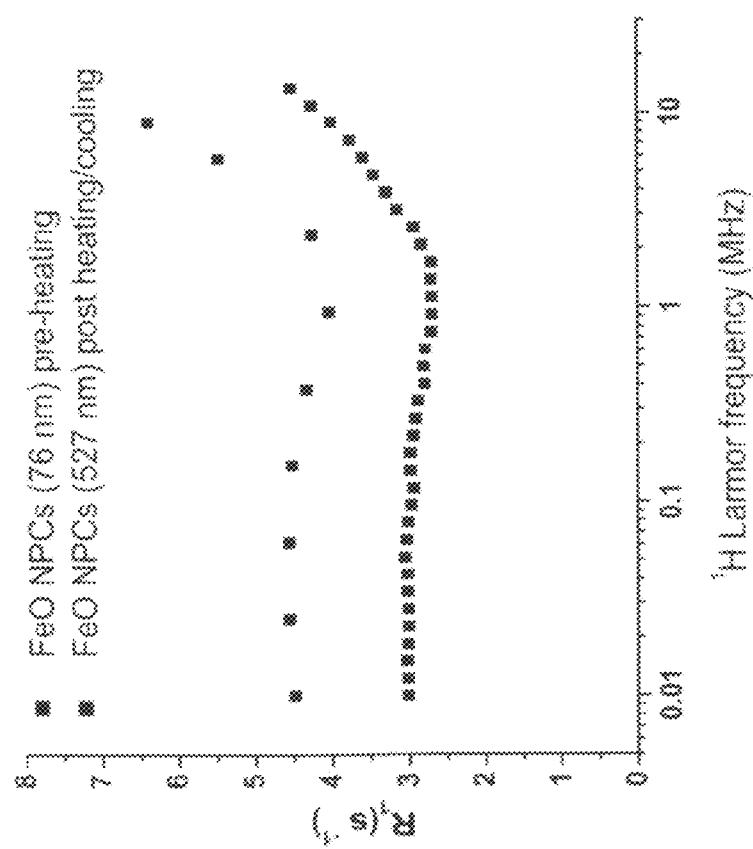

FIGS. 4A and 4B show the comparable effects of heating on the stability of the generated nanoparticle clusters where it is evident that the heating has no affect on the average size, size distribution or magnetic resonance properties of the nanoparticle clusters fabricated from the nanoparticles of the first and second type. It is evident from comparison of FIGS. 4A and 4B, and the data presented in Tables 1 and 2, that the provision of the secondary nanoparticle, in this exemplary instance Au NPs significantly improve the stabilization of the clusters. This is manifested in:
  (i) Extended lifetimes of the suspensions; the NMR and DLS responses are stable for weeks (as opposed to days for FeO NPCs).
  (ii) Improved thermal stability. The Au—FeO NPC suspensions can be heated to 60° C. for 40-60 minutes and the NMR and DLS response is fully recovered on returning to room temperature.
  (iii) Stability to dilution into the sub-millimolar range (Fe concentration).

It will be appreciated that suspension in aqueous media is necessary for biomedical applications, and most phase transfer protocols depend on transfer across a phase boundary or drying prior to resuspension. Given the stability of the nanoparticle clusters described herein it is evident that the latter approach may be applied to the production of size-controlled Au—FeO NPCs in aqueous suspension.

Heretofore the formation of nanoparticle clusters has been described with reference to clusters formed from first and second types of nanoparticles, specifically FeO and Au. In the described process preparation of magnetic fluids comprising monodisperse fatty acid stabilized magnetite nanoparticle clusters, surface decorated with Au NPs, with size control in the size range 20-150 nm has been described. These nanocomposites, i.e. clusters of first and second types of nanoparticles, have improved stability and consist of quasi-spherical clusters. It will be noted that the specific combination of FeO and Au nanoparticles to form such nanocomposites should be taken as exemplary of the type of nanocomposites that may be provided in accordance with the present teaching. In this way the teaching can be extended to other types of metal, metal-oxide, or polymer nanoparticles and their use in attenuation of NPC growth. Desirably, these secondary nanoparticles are stabilized under solvophilic conditions.

Figure 5:
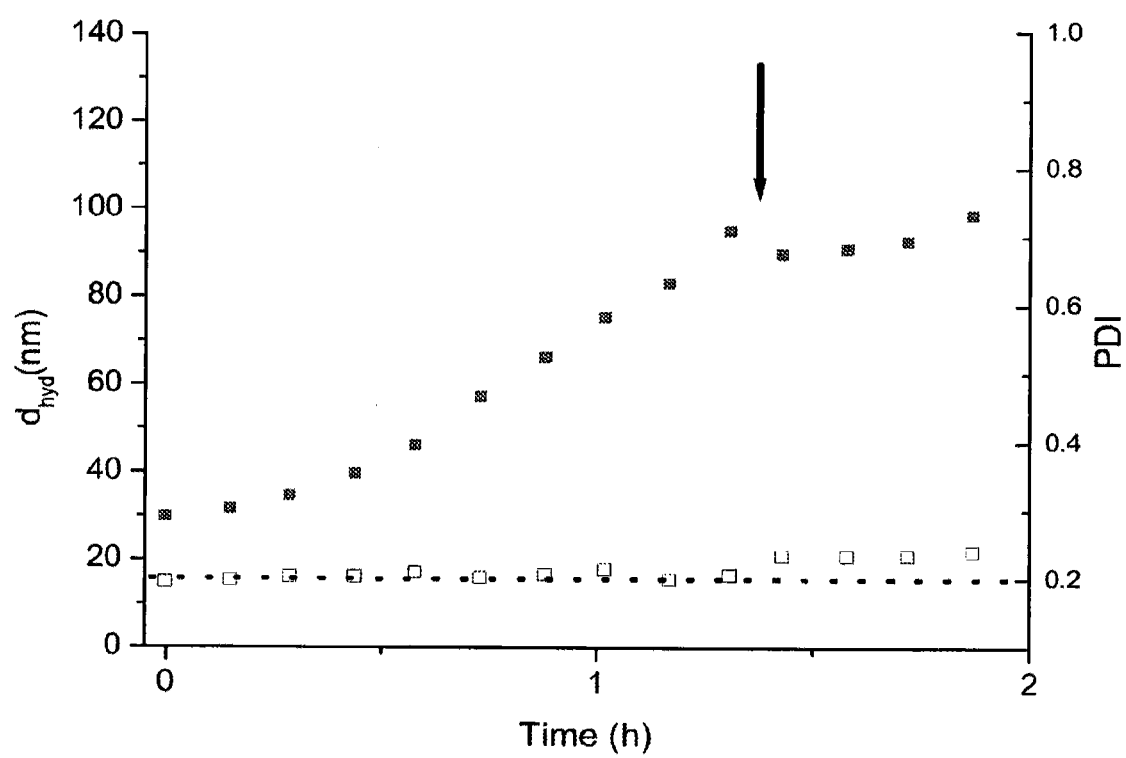
FIG. 5 shows a growth curve for FeO NPC growth over CN-modified silica stopped by addition of a suspension of oleic acid/oleylamine stabilized CoFe NPs with the time of addition indicated with an arrow.

As evidence of the general applicability of cluster formation, FIG. 5 shows how the attenuation of NPC growth may be effected by the addition of oleic acid/oleylamine stabilized cobalt ferrite nanoparticles. These CoFe NPs, which have very high magnetic anisotropy, have advantageous effects on the magnetic properties of the clusters and the magnetic resonance properties of the resulting suspensions.

Figure 6:
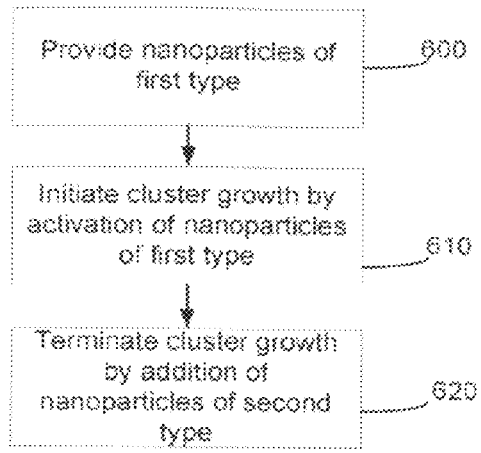
FIG. 6 shows an exemplary process flow for growth of nanoparticle clusters in accordance with the present teaching.
Figure 6A:
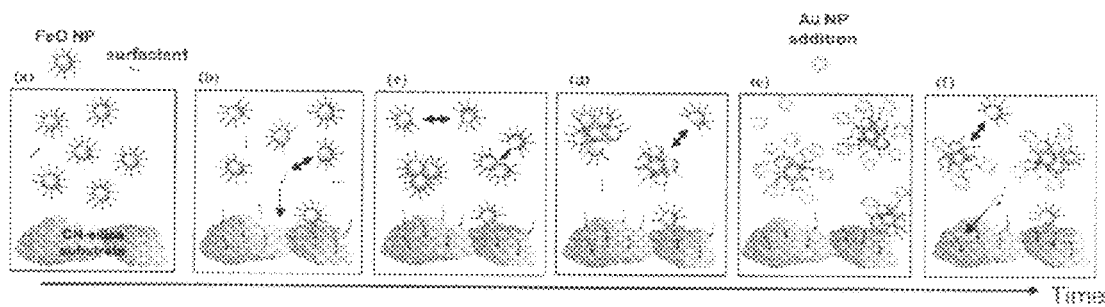
FIG. 6a shows an accompanying graphical schematic to the process flow of FIG. 6.

The mechanism described herein may be considered in terms of the steps outlined in FIG. 6. In a first step, primary nanoparticles of a first type are provided (Step 600). These are allowed to cluster together to form nanoparticle clusters (Step 610). Such an arrangement may follow the teaching of our co-assigned patent application WO 2008071742. Once a desired size distribution is met, introduction of nanoparticles of a second type (Step 620) effects an attenuation of the growth by formation of a nanoparticle cluster having nanoparticles of the first and second type. This attenuation could be of such a level as to terminate the growth completely or the concentration or ratio of the second added type may be such as to allow the growth rate to continue at the previous rate. In such a latter scenario growth of the clusters could be controlled by access to an activating agent such as those described before. In such an arrangement, further growth may be stopped or retarded by removing the suspension from contact with the activating agent. FIG. 6a shows in schematic graphical form a process such as that outlined in FIG. 6. In steps (a) and (b) FeO nanoparticles coated with a surfactant and provided in suspension are surface activated through contact with an activating agent, in this specific example—silica. In steps (c) and (d) there is shown how these activated nanoparticles may combine with one another with a resultant formation of clusters. In step (e) with the addition of Au NPs which interact with the nanoparticle cluster surface, the cluster becomes an entity fabricated from nanoparticles of first and second types: FeO and Au respectively. In step (f) it is shown how if the Au NP layer is not complete these clusters may continue to be activated by silica with continued growth of clusters.

Figure 7:
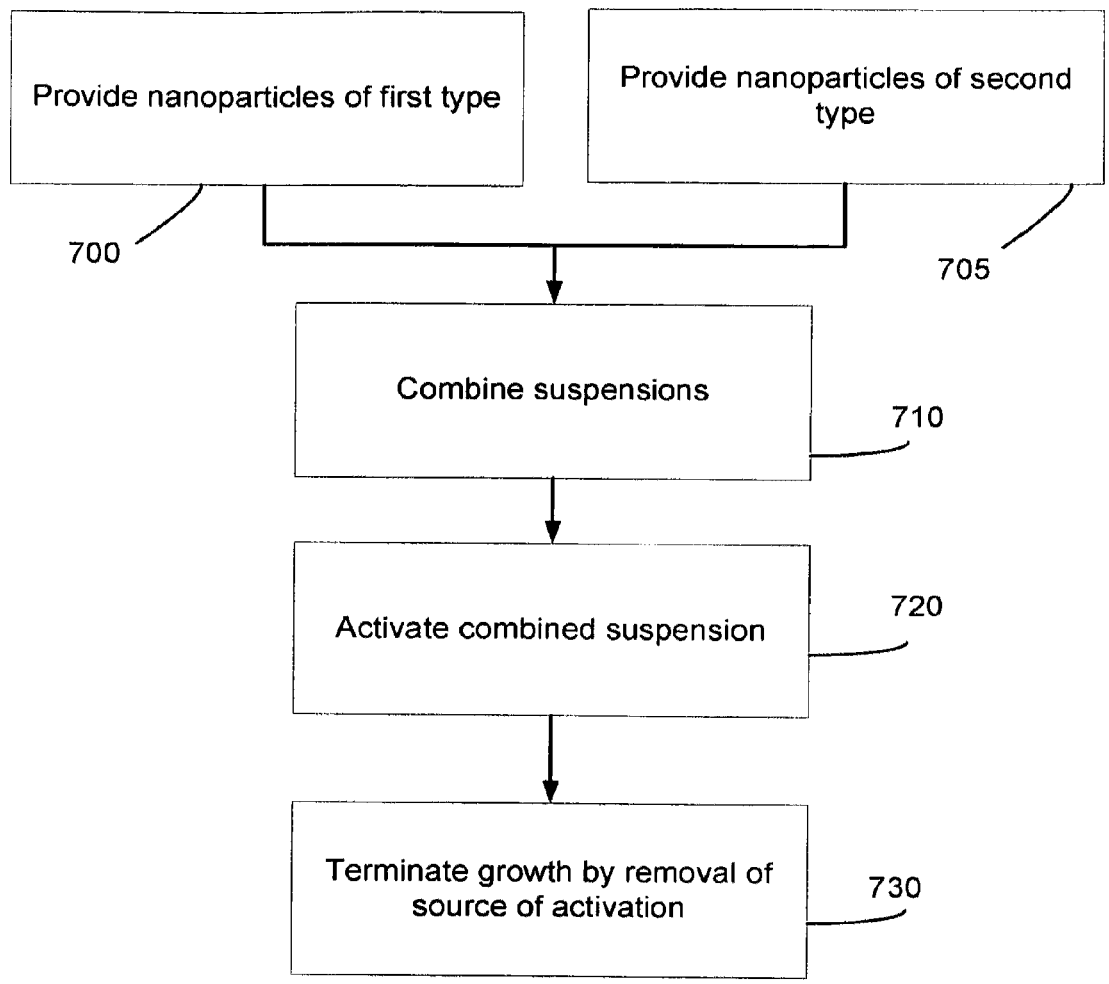
FIG. 7 shows another exemplary process flow for growth of nanoparticle clusters in accordance with the present teaching.

In an alternative process shown in FIG. 7, the primary nanoparticles of the first and second type are provided at the beginning of the methodology-Step 700, 705. These are then combined into a suspension having both types co-present (Step 710). By activation of that suspension, for example by bringing it into contact with an activating substrate such as C18 silica, cluster growth may be initiated (Step 720). Removal of the activating source or, as will be appreciated from later discussion addition of another type of NP or molecule, will result in a termination of the cluster growth (Step 730). It will be appreciated that this process or method for termination of the growth or stabilisation of the formed clusters is exemplary of the techniques that may be employed and it is not intended to limit the present teaching to any one specific mechanism except as may be deemed necessary in the light of the appended claims which follow. For example addition of a nanoparticle of a third type—such as for example a biomolecule—could also be used to stabilise the nanoparticle clusters formed, this time the stabilisation being effected by inclusion in the nanoparticle cluster of nanoparticles of this third type. In a process such as that shown in FIG. 7, whereby the first and second types of nanoparticles are introduced concurrently at the beginning of the process, the form of the final nanoparticle cluster may be such as to have each of the first and second types intermixed within the cluster structure as opposed to having one type surface decorating the outer surface of the final cluster structure.

Figure 8:
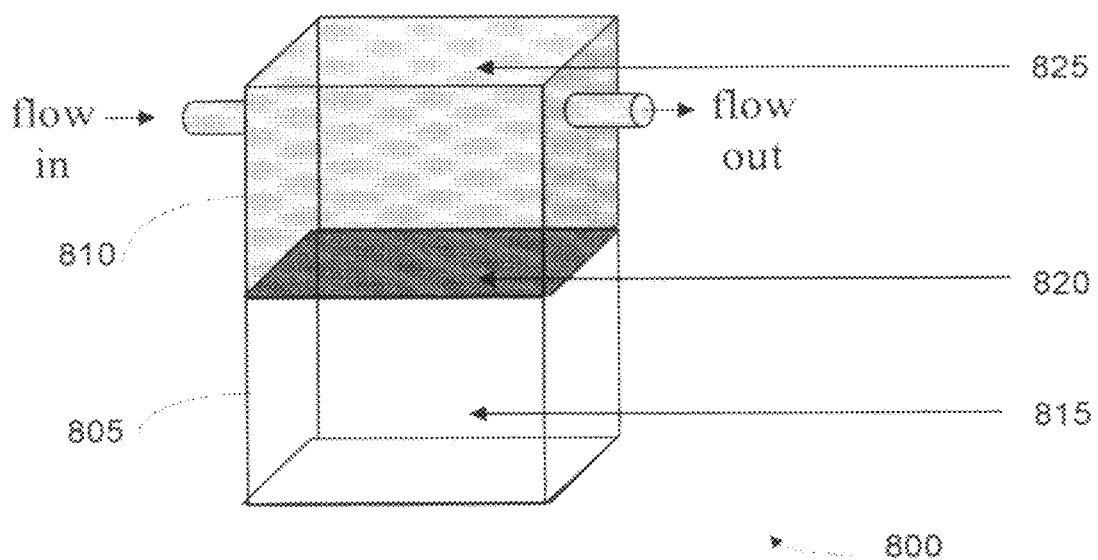
FIG. 8 shows a flow through cell that may be used in another process for growth of nanoparticle clusters in accordance with the present teaching.

In a further modified process shown in FIG. 8, a flow through arrangement is provided whereby a cell 800 comprising upper 805 and lower 810 compartments is provided. A NP suspension 815 is held in the lower compartment 805. This could be a suspension of nanoparticles of the first type only, a suspension of nanoparticles of the first and second types or nanoparticles of the second type could be introduced into this chamber at any time by appropriate means. A dialysis membrane 820 is provided to separate the upper and lower compartments and allows exchange of surfactant from the lower compartment with the upper chamber. The membrane is configured not to allow the transfer of nanoparticles or nanoparticle clusters between the two compartments. The upper compartment or chamber contains a solvent 825 either as a pure liquid or as a solution of the surfactant. By controlling the concentration of surfactant in the upper chamber and/or the rate of flow of the liquid into this chamber, the concentration of surfactant in this chamber can be adjusted, so altering the rate of transport of surfactant from the lower chamber. This will lead to surface activation of the nanoparticles or nanoparticle clusters leading to cluster growth, a process defined herein as competitive stabilizer desorption. By continuous monitoring of the size of the suspended particles in the lower chamber, e.g. by DLS (performed inside or outside the chamber) the process conditions could be optimised to control NPC growth. In modifications to that described, a feedback process may be provided with the application of computer learning techniques so as to dynamically modify the process parameters. It will be appreciated that the geometry of the cell illustrated with for example the NPC suspension provided in the lower compartment is exemplary of the type of cell arrangement that may be employed. However it will be appreciated that this arrangement is advantageous in that the dialysis membrane will not be blocked by any precipitating particles.

Figure 9:
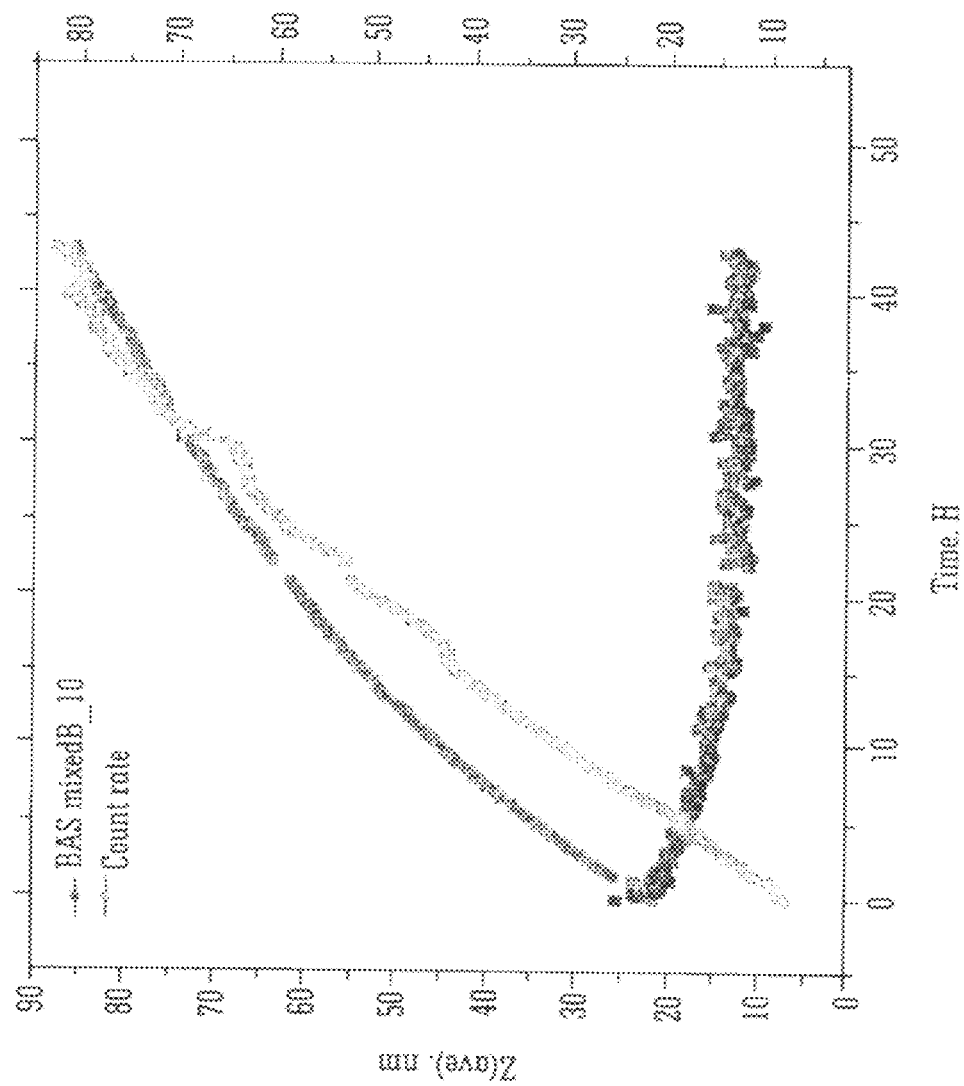
FIG. 9 shows the formation of NPCs of oleic acid stabilised NPs in $CHCl_3$, over silica-CN

FIG. 9 shows experimental data demonstrating that iron oxide NPs in $CHCl_3$ suspension, prepared using the Pinna method [N. Pinna, S. Grancharov, P. Beato, P. Bonville, M. Antonietti, M. Niederberger, Chem. Mater. 2005, 17, 3044-3049] and stabilised with oleic acid can also be assembled into NPCs by competitive stabiliser desorption in accordance with the present teaching. As is seen both the mean hydrodynamic size, or Z(ave), and the count rate are seen to increase with time. The polydispersity index, or PDI, value is also plotted, in this case multiplied by 100. The PDI is seen to decrease significantly as the hydrodynamic size increases.

In this example, the originating NPs are synthesised and stabilised with a temporary ligand, which is subsequently replaced with oleic acid. Hence the quantity of oleic acid can be very precisely controlled and the reproducibility of the process is improved from preparation to preparation.

A second advantage of such an approach is that the polydispersity of the cluster suspension actually improves as the process proceeds. It will be appreciated by those of skill in the art that dynamic light scattering provides a PDI value, which is an accepted measure of the width of the hydrodynamic size distribution. In discussion heretofore, this value stayed more or less constant at c. 0.20, demonstrating that the cluster size distribution was comparably broad to the initial nanoparticle size distribution. In accordance with this methodology, the PDI decreases from initial values of 0.15-0.20 (representing the size distribution of the primary nanoparticles) down to 0.10 to 0.15. A narrower size distribution is advantageous in that the usage or application of the generated NPCs can be tailored based on the size distribution of clusters within a particular suspension.

A third advantage is that the yield from the process is considerably improved. As was discussed above, precipitation of the NPs and NPCs is an ongoing process. Using a methodology such as that exemplified with the schematic of FIG. 9, the rate of the process may be controlled, and in addition a higher concentration is maintained throughout. Furthermore, the process is very reproducible. Yields are significantly in excess of 70%, at a size of 80 nm.

It will be appreciated that the solvent used in this exemplary arrangement is a polar solvent, $CHCl_3$. Heretofore, the examples described have used oleic acid alkyl chains in a heptane medium. It will be appreciated that the use of $CHCl_3$ demonstrates that 'absolutely solvophilic' conditions are not required and as such that polar and non-polar solvents may be used within the context of the present teaching.

Figure 10:
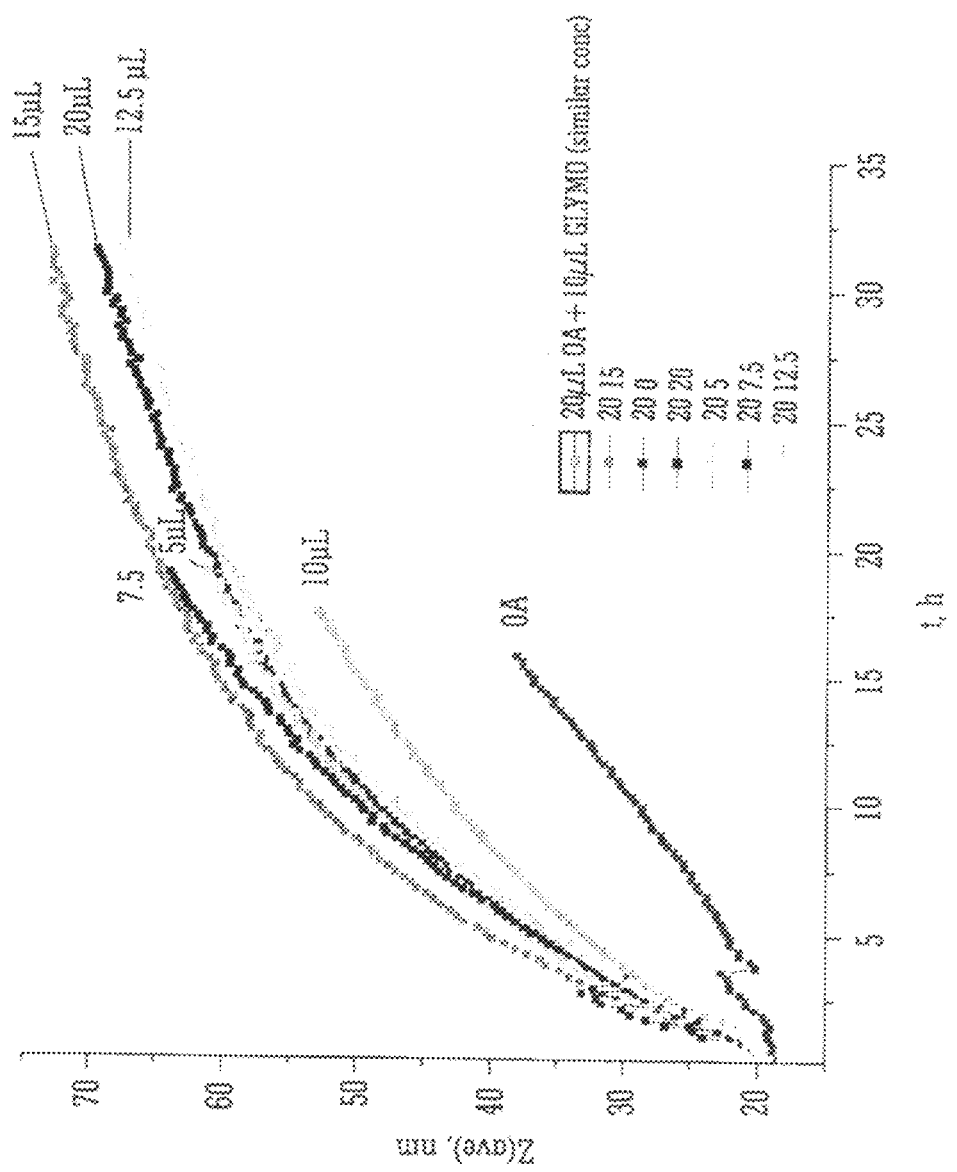
FIG. 10 shows the formation of NPCs formed from separate mixtures of oleic acid stabilised NPs and GLYMO stabilised NPs in $CHCl_3$, over silica-CN

In the examples prior to FIG. 9 the first and second type were exemplified by FeO being representative of the nanoparticles of the first type and Au or CoFe representative of nanoparticles of the second type. In the example of FIG. 10, where FeO is a constituent in each of the two types, it can be seen that increasing the content of the GLYMO stabilised NPs alters the growth kinetic significantly. Specifically by coating the FeO particles with different surfactant molecules it is possible to distinguish between the two types—even though each type comprises FeO.

In accordance with the present teaching it is possible generate NPCs from suspensions of more than one type of nanoparticle. As the FeO coated with oleic acid and the FeO coated with GLYMO are distinguishable from one another they may be considered nanoparticles of first and second types within the context of the present teaching. In one example assembled clusters were generated using a mixture of two types of iron-oxide NPs; surface stabilised with oleic acid and with GLYMO. GLYMO will be appreciated is an example of bifunctional organosilane having a chemical formulation of (3-glycidyloxypropyl)trimethoxysilane. These $CHCl_3$ suspensions were prepared by splitting a single NP suspension (from the Pinna method) and replacing the temporary ligand either with oleic acid or with GLYMO. GLYMO will be appreciated is an example of a ligand suitable as an initiator for a ring opening reaction to bind any one of a range of polyelectrolyte stabilisers, which will facilitate phase transfer into water.

FIG. 10 demonstrates that by controlling the relative concentrations of the two types of NPs the kinetics of cluster growth can be tuned. This data shows that the present teaching may be used to form clusters containing both oleic acid and GLYMO stabilised NPs which it will be appreciated is an example of nanoparticle clusters formed from individual nanoparticles of two types, each of which has different functionality. It will be appreciated that ligands other then GLYMO, that perform similar functions and that NPs with other functionalities could be used. Such functionalities could be used to improve stability, to initiate polymerization, to bind to a polymer, to bind to a marker entity, or to bind a biomolecule. They could also be used to provide a linker group which could itself be used to provide any such functionalities In addition NPCs could be assembled from NPs, each of which is stabilised by a mixture of OA and GLYMO ligands. In another arrangement, the NPs of different types may each be stabilized by a combination of a surfactant that are subject to competitive stabilizer desorption and other ligands bearing appropriate chemical functionalities. In this way a surfactant molecule within the context of the present teaching can be considered as one that binds to the surface of the nanoparticle to stabilize it but which can be removed to provide a reactive nanoparticle.

It should be noted that the same surfactant could be used for each of the first and second types of nanoparticles—the first and second types then being distinguishable due to the presence and/or identity of the different functional groups included in each type. In this way the nanoparticles of the first and second type can be considered as being first and second types if they are distinguishable prior to their combination.

What has been described herein are exemplary methodologies for the preparation of flexible assemblies of magnetic nanoparticle and nanoparticle composites of controlled size and tuneable composition with potential applications in chemistry, biology and medicine. The exemplary binary colloidal nanocomposite materials have been shown to have controlled growth throughout the growth process. The characterization of exemplary stable heptane suspensions by dynamic light scattering, NMR and TEM has been shown. It is evident from the described use of DLS for characterizing the nanocomposites in suspension that the z-, or number average, hydrodynamic size, $(d_{hyd})$, and the PDI, or polydispersity index, values in the range 0.1-0.2 that the produced nanoparticle clusters are provided in a monodisperse suspension. The generated or fabricated nanoparticle clusters of first and second types of nanoparticles exhibit a robust stability to exposure to varying concentrations, heating and temporal delay. Arising from this robustness, these clusters are suitable for phase transfer and may be advantageously employed in a number of chemical, biological and medicinal applications.

While the present teaching has been exemplified with reference to the growth of clusters comprising as a first constituent FeO, it will be appreciated that this is exemplary of the type of nanoparticle that exhibits strong magnetic effects and is therefore particularly advantageous when employed in medicinal applications where such behaviour allows for its use as a contrast agent, hyperthermia mediator, or in drug delivery. It should be noted that development of size-controlled magnetic NPCs for biomedical application requires colloidal stability in physiological media. In accordance with the present teaching the formed nanoparticle clusters may be surface functionalised and phase transferred into water as was outlined above with regard to the data presented on stability of the nanoparticle clusters to drying and then re-suspension into solution.

It is believed that the first and second particles combine with one another through physisorption as opposed to chemically linking or bonding of the particles to one another. However, the teaching is not to be construed as being limited to the exemplary types of nanoparticles or the mechanism for combination of the nanoparticle cluster from the particles of the first and second types as modifications can be made to that described herein without departing from the spirit or scope of the present teaching which is to be construed as limited only insofar as is necessary in the light of the claims which follow.

It will be appreciated and understood that traditional methods for producing size-controlled magnetic NPCs usually involve the in situ formation and stabilization of the NPs in the presence of polymers or the addition of polymers to existing NPs. In these prior art arrangements there are a number of factors that can affect the ultimate dimensions of the formed nanoparticle clusters. For example, the size of aggregates formed may be influenced by the fractional coating of the nanoparticle cores and the surface chemistry of the polymer used for stabilisation. There are therefore limitations in these prior art approaches arising from nanoparticle loading and the individual chemistries employed.

In accordance with the present teaching, previously stable nanoparticle suspensions are perturbed by the introduction of a tertiary phase or external activating agent that competes for the stabilizer. Under appropriate conditions this produces continuous growth of monodisperse NPCs over a period of hours. Effectively this method introduces an instability of external origin that drives cluster formation. The resulting advantage is in the temporal nature of the controlled growth; which allows external interventions, such as the removal of the instability, to be made at a selected time. This is in contrast with prior art techniques which have difficulties in producing stable clusters arising from the fact that the nanoparticles must be unstable themselves for clustering to occur, hence the resulting clusters are only marginally stable. In addition using the techniques of the present teaching, the size of the primary NPs can be selected, by a number of methods, as the initial suspension is stable.

While the present teaching has been exemplified with reference to FeO as the nanoparticle of the first type and either Au or CoFe as the nanoparticle of the second type it will be appreciated that these are provided as specific non-limiting examples of the types of nanoparticles that could be combined into nanoparticle clusters in accordance with the present teaching. Furthermore the same base material can be used for each of the first and second types but by providing a different surfactant molecule on the same base material—as was discussed with reference to FIG. 9—it is possible to distinguish between the first and second types.

Using a definition of a nanoparticle as being any particle having one dimension less than 100 nanometers, it will be appreciated that molecules and bio-organic material could be equally considered as a nanoparticle within the present context. In this way bio-molecules could be considered a nanoparticle of a second type which can be clustered with the nanoparticles of the first type for generation of the nanoparticle clusters in accordance with the present teaching. Use of such a bio-molecule provides advantages in that the specifics of the bio-molecule chosen could be optimised for specific molecular targeting or the like. While the clusters will comprises nanoparticles of the first and second types, certain applications may require nanoparticles of a third type to be clustered with the first and second types of nanoparticles in the nanoparticle cluster. This third type of nanoparticle could be introduced into the process to stabilise the nanoparticle cluster of the first and second types or could be introduced prior to stabilisation. As such the present teaching may be considered as encompassing formation of nanoparticle clusters of a generalised form as long as the cluster is formed from at least identifiable particles of first and second types of nanoparticles and also includes surfactant molecules which may be competed for by an alternative phase to effect surface activation of the nanoparticles or nanoparticle clusters.

It will be appreciated that when discussing the nanoparticles of the first and second types, that the second type of nanoparticles within the context of the present teaching does not necessarily include surfactant or other stabilizing agents which are used to stabilise the nanoparticles of the first type prior to generation of the nanoparticle clusters. The nanoparticles of the second type in this way are distinct and different to the nanoparticles of the first type. The resultant structure of the nanoparticle cluster comprises both individual nanoparticles of the first and second type and constituents of the surfactant that was originally used to stabilize the nanoparticles in suspension. It is the presence of the surfactant which on activation by the external activation agent resulted in an active nanoparticle that combined with another activated nanoparticle or nanoparticle cluster to form the nanoparticle clusters of the present teaching. It will be understood that when evaluating the properties of nano-dimensioned particles that the dimensions of the particles have significant affects on the properties of the particles. In the context of a cluster formation such as provided in accordance with the present teaching, the NPCs formed from smaller NPs will tend to have properties associated with the smaller NPs, as opposed to those of larger NPs.

Fabricated nanoparticle clusters as provided in accordance with the present teaching have a plurality of applications and uses. For example, the clusters may be used in a biomedical application by introducing the formed nanoparticle clusters into the body. Alternatively, they could be used as a drug delivery agent, by encapsulating the one or more nanoparticle clusters within a heat sensitive medium, the heat sensitive medium providing a carrier for pre-defined pharmaceutical compositions. Such a drug delivery agent could be used for delivering a pharmaceutical composition within a body, by introducing the agent to a body and then causing a generation of heat within the agent through stimulation of the one or more nanoparticle clusters for therapeutic purposes or to effect disruption of the agent and the release of pharmaceutical composition. The stimulation of the nanoparticle clusters could be achieved through at least one of:

a. Applying a static magnetic field to the area where the agent is located, b. Applying an RF field to the area where the agent is located, c. Using a laser to target the area where the agent is located.

In such an arrangement the static field provides for a localisation of the nanoparticle clusters at a defined location, the RF field provides for a heating of the nanoparticle clusters and the laser provides for a heating of the nanoparticle clusters.

The clusters if formed of magnetic materials could also be used as a contrast agent. Another application of the clusters would be as a mediator for assisting in hyperthermia treatments or for use in forming a catalyst. In such a latter arrangement the catalyst would desirably comprise one or more nanoparticle clusters formed on a surface of a substrate, and the method would include:

applying the formed nanoparticle clusters onto the surface of a substrate, and annealling the applied nanoparticle clusters to provide for a thermal desorption of adsorbed species from the applied nanoparticle clusters.

Therefore it will be appreciated that a methodology for fabrication of a nanoparticle cluster comprising distinct nanoparticles of a first and second type has been described. These clusters have application in a plurality of different fields and it is not intended to limit the present teaching to any one specific field as modifications can be made to that described herein without departing from the scope of the invention which is to be limited only insofar as is deemed necessary in the light of the claims which follow.

The words comprises/comprising when used in this specification are to specify the presence of stated features, integers, steps or components but does not preclude the presence or addition of one or more other features, integers, steps, components or groups thereof.

The invention claimed is:

1. A method of forming nanoparticle clusters of nanoparticles of at least a first and a second type, the method comprising:
    a. providing in a first step, a plurality of individually coated nanoparticles of a first type in suspension, the nanoparticles being coated with a plurality of surfactant molecules;
    b. providing in a second step, a plurality of nanoparticles of a second type into the suspension of nanoparticles of the first type, the second type being different from the first type;
    c. surface activating individual ones of the plurality of nanoparticles of the first type by desorption of surfactant molecules from the surface of the coated nanoparticles through exposure of individual ones of the plurality of nanoparticles of the first type to an activating agent;
    d. allowing, through the expiration of time, activated nanoparticles to combine to form clusters of nanoparticles through a physical interaction, and
    e. terminating the formation of nanoparticle clusters by one of bringing the plurality of nanoparticles of the second type into contact with the nanoparticles of the first type, or removing the suspension from contact with the activating agent, or introducing nanoparticles of a third type into the suspension, and
    wherein the formed nanoparticle clusters comprise nanocomposites with identifiable individual nanoparticles of the first type, individual nanoparticles of the second type and surfactant molecules.

2. The method of claim 1, wherein the dimensions of the formed clusters are determined by the timing of the bringing the plurality of nanoparticles of the second type into contact with the nanoparticles of the first type.

3. The method of claim 1 wherein the plurality of nanoparticles of the second type are brought into contact with the nanoparticles of the first type prior to the growth of clusters of nanoparticles of the first type.

4. The method of claim 1 wherein the plurality of nanoparticles of the second type are brought into contact with the nanoparticles of the first type after the growth of clusters of nanoparticles of the first type.

5. The method of claim 1 wherein the dimensions of the formed clusters are determined by the timing of removal of the suspension of nanoparticles of the first type from contact with the activating agent.

6. The method of claim 1 wherein the growth of the nanoparticle clusters within the suspension is monitored to determine an appropriate time for termination of said growth.

7. The method of claim 6 wherein the monitoring is a continuous process or is effected over a plurality of iterations.

8. The method of claim 1 wherein the termination of formation of the nanoparticle clusters is effected after expiration of a predefined time period.

9. The method of claim 1 wherein the activating agent is a substrate.

10. The method of claim 9 wherein the substrate is a silica substrate.

11. The method of claim 10 wherein the silica substrate is formed from grafted silica.

12. The method of claim 1 provided in a flow through arrangement whereby dialysis across a membrane affects a reduction in the concentration of a stabilised suspension resulting in generation of activated nanoparticles and growth of nanoparticle clusters.

13. The method of claim 1 wherein the suspension is provided in a flow through arrangement.

14. The method of claim 1 wherein the suspension includes magnetic nanoparticles.

15. The method of claim 1 wherein the suspension includes fatty-acid coated nanoparticles.

16. The method of claim 15 wherein the nanoparticles of the first type are iron-oxide nanoparticles.

17. The method of claim 1 wherein the nanoparticles of the first and second type are coated with surfactant molecules, the surfactant molecules coating the nanoparticles of the first type differing from those coating the second type.

18. The method of claim 17 wherein the nanoparticles forming the nanoparticles of the first type are the same as the nanoparticles forming the nanoparticles of the second type, the surfactant coating applied to each of the first and second types being different.

19. The method of claim 1 wherein the surfactant comprises at least one of oleic acid or GLYMO.

20. The method of claim 1 comprising re-activating a previously stabilised nanoparticle cluster to prepare size-controlled nanostructures with a radially variable or multi-layered composition.

21. The method of claim 1 including stabilizing the nanoparticle clusters and wherein the stabilizing provides for:
   a) a cross-linking and phase transfer of the nanoparticle clusters into a stable aqueous solution, or
   b) an embedding of the clusters in a polymer matrix, or
   c) encapsulating the clusters with suitable amphiphilic molecules, such as a lipids.

22. The method of claim 1 wherein the nanoparticles of the second type are bio-molecules.

23. The method of claim 1 wherein the terminating the formation of nanoparticle clusters comprises introducing nanoparticles of a third type into the suspension, the nanoparticles of the third type being bio-molecules.

24. A method of forming nanoparticle clusters comprising:
   a. providing oleate stabilised magnetic nanoparticles of a first type in a suspension,
   b. effecting a desorptive loss from the surface of the nanoparticle of a previously temporarily adsorbed oleate molecule on the nanoparticle's surface so as to form a surface activated reactive nanoparticle through exposure to an external activating agent,
   c. stabilising the surface activated reactive nanoparticle through physical interaction and combination with other reactive nanoparticles and the provision of a plurality of nanoparticles of a second type into the suspension, the second type being different from the first type, the stabilisation resulting in the formation of clusters comprising nanocomposites with identifiable individual nanoparticles of the first and second type.

25. The method of claim 24 wherein the surface activated nanoparticles are activated through interaction with a substrate.

26. The method of claim 25 wherein the interaction is through an adsorption process whereby capping molecules from the nanoparticles are adsorbed onto the surface of the substrate.

27. A method of using nanoparticle clusters in a biomedical application, the method including:
   a. forming one or more nanoparticle clusters in accordance with the method of claim 1,
   b. introducing the formed nanoparticle clusters into the body.

28. A method of forming a drug delivery agent, the method including of:
   a. forming one or more nanoparticle clusters in accordance with the method of claim 1, and
   b. encapsulating the one or more nanoparticle clusters within a heat sensitive medium, the heat sensitive medium providing a carrier for a predefined pharmaceutical compositions.

29. A method of delivering a pharmaceutical composition within a body, the method including the formation of a drug delivery agent as claimed in claim 28, introducing the agent to a body and then causing a generation of heat within the agent through stimulation of the one or more nanoparticle clusters for therapeutic purposes or to effect disruption of the agent and the release of pharmaceutical composition.

30. The method of claim 29 wherein the stimulation of the nanoparticle clusters is achieved through at least one of:
   a. applying a static magnetic field to the area where the agent is located,
   b. applying an RF field to the area where the agent is located,
   c. using a laser to target the area where the agent is located.

31. The method of claim 30 wherein the static field provides for a localisation of the nanoparticle clusters at a defined location.

32. The method of claim 31 wherein the RF field provides for a heating of the nanoparticle clusters.

33. The method of claim 31 wherein the laser provides for a heating of the nanoparticle clusters.

34. A method of forming a contrast agent comprising magnetic nanoparticle clusters comprising the method of claim 1.

35. A method of forming a mediator for assisting in hyperthermia treatments comprising the method of claim 1.

36. A method of forming a catalyst, the catalyst having one or more nanoparticle clusters formed on a surface of a substrate, the method including:
   a. providing one or more nanoparticle clusters in accordance with the method of claim 1,
   b. applying the formed nanoparticle clusters onto the surface of a substrate, and
   c. annealing the applied nanoparticle clusters to provide for a thermal desorption of adsorbed species from the applied nanoparticle clusters.

37. A method of forming clusters of nanoparticles, the formed clusters having individual and distinct nanoparticles of at least a first and a second type, the method comprising:
   a. providing a plurality of nanoparticles of a first and of a second type in a suspension, the first type being different from the second type, the individual nanoparticles of at least one of the nanoparticles of the first or second type being stabilised through provision of a plurality of surfactant molecules on their surface;
   b. effecting a desorption of the surfactant molecules from the surface of the nanoparticles to surface activate individual ones of the plurality of nanoparticles, the desorption being effected through exposure of individual ones of the plurality of nanoparticles to a physical activating agent;
   c. allowing, through the expiration of time, activated nanoparticles to combine to form clusters of nanoparticles; and
   d. stabilising the formed nanoparticle clusters, the formed nanoparticle clusters comprising nanocomposites with identifiable individual nanoparticles of the first type, individual nanoparticles of the second type and surfactant molecules.

* * * * *